United States Patent
Uemura et al.

(10) Patent No.: US 6,465,681 B2
(45) Date of Patent: Oct. 15, 2002

(54) PRODUCTION PROCESS FOR HYDROXYALKYL (METH)ACRYLATE

(75) Inventors: Masahiro Uemura, Himeji (JP); Tokumasa Ishida, Himeji (JP); Yukihiro Yoneda, Himeji (JP); Tetsuya Kajihara, Himeji (JP); Yasuhiro Shingai, Himeji (JP); Tadayoshi Kawashima, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/021,061

(22) Filed: Dec. 19, 2001

(65) Prior Publication Data

US 2002/0082443 A1 Jun. 27, 2002

(51) Int. Cl.$^7$ .......................... C07C 67/26; C07C 69/52; C07C 69/00
(52) U.S. Cl. .................. 560/205; 560/129; 560/205
(58) Field of Search ................ 560/209, 129, 560/205

(56) References Cited

FOREIGN PATENT DOCUMENTS

| JP | 51133227 | 11/1976 |
|---|---|---|
| JP | 52023019 | 2/1977 |
| JP | 646182 | 2/1989 |
| JP | 10237021 | 9/1998 |
| JP | 10237022 | 9/1998 |

*Primary Examiner*—Alan L. Rotman
*Assistant Examiner*—Hector Reyes
(74) *Attorney, Agent, or Firm*—Roylance, Abrams, Berdo & Goodman, L.L.P.

(57) ABSTRACT

The present invention provides: a production process for a hydroxyalkyl(meth)acrylate, which can raise productivity together with avoiding danger of explosion, and further can suppress side-formation of impurities such as a diester or a monoester wherein the impurities have a bad influence on product quality. When the time from the start of adding an alkylene oxide (AO) till the end of supplying the entirety of the AO is defined as T (hour), the amount of more than 50% of the entirety of the AO is supplied before T/2 (hour) has passed since the start of adding the AO. In addition, when the total amount of an AO as supplied and the time from the start of adding the AO till the end of supplying the entirety of the AO are defined as W (mol) and T (hour) respectively, the supply of the AO is started at a supplying speed V0 (mol/hour) that is faster than the average supplying speed V (=W/T) (mol/hour), and thereafter the supplying speed of the AO is decreased at least once, and then the supply of the entirety of the AO is completed for T (hour) from the start of adding the AO.

5 Claims, No Drawings

PRODUCTION PROCESS FOR HYDROXYALKYL (METH)ACRYLATE

BACKGROUND OF THE INVENTION

A. Technical Field

The present invention relates to a production process for a hydroxyalkyl(meth)acrylate, which comprises the step of carrying out a reaction between (meth)acrylic acid and an alkylene oxide.

B. Background Art

When a hydroxyalkyl(meth)acrylate is produced by carrying out a reaction between (meth)acrylic acid and an alkylene oxide, impurities, such as a diester (for example, alkylene glycol di(meth)acrylate) and a monoester (for example, dialkylene glycol mono(meth)acrylate), are formed as by-products. Therefore, a problem of lowering the reaction selectivity of the hydroxyalkyl(meth)acrylate is hitherto caused.

This diester promotes the polymerization of the aimed hydroxyalkyl(meth)acrylate and causes a trouble such as clogging of apparatuses. In addition, when a (co)polymer was produced by using a hydroxyalkyl(meth)acrylate including a diester as a raw material, the resultant polymer might have "turbidity" or be gelled in the polymerization. Furthermore, the vapor pressure of this diester approximate that of the hydroxyalkyl(meth)acrylate. Therefore, once the diester is formed, it is very difficult to separate them.

It is known that the diester is formed by an esterification or disproportionation reaction as a side-reaction when a reaction liquid obtained by the reaction between (meth) acrylic acid and an alkylene oxide is heated to higher temperature (JP-A-133227/1976). Therefore, if the reaction temperature is lowered, the formation of the diester is suppressed. However, if the reaction temperature is lowered, the productivity is not only lowered because the reaction process time is extremely lengthened but also a portion of the resultant product may be denatured or decomposed because of the reaction for a long time.

In addition, methods for adding an inhibitor for forming the diester are proposed (JP-A-133227/1976, JP-A-23019/1977, JP-A-237021/1998, and JP-A-237022/1998). However, the sufficient effect is not obtained.

In addition, as to the monoester, methods for suppressing its formation are proposed (JP-B-6182/1989). However, the sufficient effect is not obtained.

In a production process of a hydroxyalkyl(meth)acrylate by carrying out a reaction between (meth)acrylic acid and an alkylene oxide, the following modes are generally employed: a mode of adding the (meth)acrylic acid, the alkylene oxide and a catalyst all at once to a reactor (addition of all at once); or a mode of beforehand charging a reactor with the (meth)acrylic acid and a catalyst, and then adding the alkylene oxide to the reactor (addition of one after another).

When the addition of all at once is carried out, the formation of the impurities is suppressed. Therefore, it is a favorable mode in the respect that the reaction selectivity of the hydroxyalkyl(meth)acrylate can be raised. However, when the alkylene oxide exists together with oxygen and a certain condition is satisfied, an explosive (mixed) gas is formed. Therefore, the addition of all at once, which causes a concentration of the alkylene oxide of the gas phase in the reaction system to rise when the raw alkylene oxide is charged or at the start of adding the alkylene oxide, has a problem of high danger of explosion.

When the addition of one after another is carried out, it is a favorable mode in the respect that the above-mentioned problem is decreased and the hydroxyalkyl(meth)acrylate can safely be produced, and further the formation of the impurities can be suppressed by selecting an appropriate reaction temperature and controlling it.

In the addition of one after another, the alkylene oxide is generally supplied at a constant speed hitherto. This is because the following is thought: it is easy to control an appropriate reaction temperature for suppressing the side-formation of the impurities; and the supply of the alkylene oxide is favorably carried out at a constant speed in consideration for difficulty of handling the alkylene oxide.

In order to raise productivity in the addition of one after another, it is necessary to increase the supplying speed of the alkylene oxide and to shorten the supplying time of the alkylene oxide. In addition, it is desired to shorten the supplying time of the alkylene oxide in order also to suppress the side-formation of the impurities (for example, the diester or the monoester) that have a bad influence on product quality. However, a conventionally general method, which involves supplying with simply increasing the supplying speed in a definite amount, causes the concentration of the residual alkylene oxide to increase, and causes a problem of danger of explosion.

SUMMARY OF THE INVENTION

A. Object of the Invention

Accordingly, an object of the present invention is to provide: a production process for a hydroxyalkyl(meth)acrylate, which can raise productivity together with avoiding danger of explosion, and further produces the hydroxyalkyl (meth)acrylate with high purity for a short time while the side-formation of impurities such as a diester or a monoester is suppressed wherein the impurities have a bad influence on product quality.

B. Disclosure of the Invention

The present inventors diligently studied in order to solve the problems. As a result, they found that the problems can be solved by varying a supplying speed of the alkylene oxide so as to adjust to specific conditions during a supplying period.

In addition, they found that the temperature-dependency of the formation amount of the diester or the monoester is varied by the reaction conversion of the (meth)acrylic acid in a reaction liquid. Then, they found that: if the alkylene oxide was added to the (meth)acrylic acid, the temperature-dependency was high at the initial reaction stage when the reaction conversion of the (meth)acrylic acid was low, but the temperature-dependency was low at the latter reaction stage when the reaction conversion of the (meth)acrylic acid was high.

According to the above findings, the present inventors reached an idea that the problems of the present invention could be solved by varying the supplying speed of the alkylene oxide during the supplying period and/or by: suppressing the formation of the diester or the monoester by controlling the reaction temperature in the range of a low temperature while the reaction conversion of the (meth) acrylic acid is low; and elevating the reaction temperature when the reaction conversion of the (meth)acrylic acid was high to a certain extent. Then, they completed the present invention.

That is to say, a production process for a hydroxyalkyl (meth)acrylate, according to the present invention, comprises the step of carrying out a reaction between (meth) acrylic acid and an alkylene oxide in the presence of a catalyst in order to produce the hydroxyalkyl(meth)acrylate, wherein: when the time from the start of adding the alkylene oxide till the end of supplying the entirety of the alkylene oxide is defined as T (hour), the amount of more than 50% of the entirety of the alkylene oxide is supplied before T/2 (hour) has passed since the start of adding the alkylene oxide.

In addition, another production process for a hydroxyalkyl(meth)acrylate, according to the present invention, comprises the step of carrying out a reaction between (meth)acrylic acid and an alkylene oxide in the presence of a catalyst in order to produce the hydroxyalkyl (meth)acrylate, wherein: when the total amount of the alkylene oxide as supplied and the time from the start of adding the alkylene oxide till the end of supplying the entirety of the alkylene oxide are defined as W (mol) and T (hour) respectively, the supply of the alkylene oxide is started at a supplying speed V0 (mol/hour) that is faster than the average supplying speed V (=W/T) (mol/hour), and thereafter the supplying speed of the alkylene oxide is decreased at least once, and then the supply of the entirety of the alkylene oxide is completed for T (hour) from the start of adding the alkylene oxide.

Furthermore, yet another production process for a hydroxyalkyl(meth)acrylate, according to the present invention, comprises the step of carrying out a reaction between (meth)acrylic acid and an alkylene oxide in the presence of a catalyst in order to produce the hydroxyalkyl (meth)acrylate, with the production process further comprising: the alkylene-oxide supplying step of mildly carrying out the reaction with maintaining a reaction temperature during the supply of the alkylene oxide in the range of 40 to 100° C.; thereafter the step of heating to a temperature higher than the reaction temperature at the end of the alkylene-oxide supplying step by at least 3° C.; thereafter the aging step of continuing the reaction at a reaction temperature not lower than the temperature after the heating step, and wherein the heating step is started when the reaction conversion of the (meth)acrylic acid is not less than 50%.

These and other objects and the advantages of the present invention will be more fully apparent from the following detailed disclosure.

DETAILED DESCRIPTION OF THE INVENTION

First of all, the outline of a production process for a hydroxyalkyl(meth)acrylate to which the production process according to the present invention is favorably applicable is explained in the following way.

In the first place, the reaction between the (meth)acrylic acid and the alkylene oxide is carried out in the presence of a catalyst. The reaction ratio of this reaction is often less than 100%, and the resultant reaction liquid at the end of the reaction generally includes residues such as unreacted (meth)acrylic acid or alkylene oxide. Therefore, the above reaction liquid is fed to a step of removing these unreacted residues of raw materials from the reaction liquid. Then, the purification is carried out by distillation as a subsequent final step with the result that the aimed hydroxyalkyl(meth) acrylate is obtained.

Hereinafter, the step of the reaction between the (meth) acrylic acid and the alkylene oxide in the presence of the catalyst, which is characteristic of the production process according to the present invention, is explained.

The alkylene oxide usable in the present invention has favorably 2 to 6 carbon atoms, more favorably 2 to 4 carbon atoms. Examples thereof include ethylene oxide, propylene oxide, and butylene oxide. Among them, ethylene oxide or propylene oxide is favorable. In addition, the (meth)acrylic acid usable in the present invention means acrylic acid or methacrylic acid.

The reaction between the (meth)acrylic acid and the alkylene oxide in the presence of the catalyst can be carried out according to methods as generally used for these kinds of reactions.

For example, when the reaction is carried out in a batch manner, it is carried out by introducing the alkylene oxide into the raw (meth)acrylic acid as charged. Then, the alkylene oxide is added one after another. That is to say, the alkylene oxide is continuously and/or intermittently added to the (meth)acrylic acid (hereinafter, they may be referred as each "continuous addition" or "intermittent addition"). Then, as is often the case with this kind of reaction, the reaction is continued still after the addition of the alkylene oxide, in other words, the aging is carried out, and thereby the reaction can be completed.

In addition, it is not always necessary to initially charge the (meth)acrylic acid at one time, and it can be divided to some portions and then added.

The addition of one after another as mentioned above means what is called a mode for not adding all at once (a mode for adding (meth)acrylic acid, an alkylene oxide, and a catalyst all at once to a reactor). The "continuous addition" means the addition of one after another, such as continuous addition little by little, and the "intermittent addition" means the addition of one after another by dividing the entirety of the amount as added into arbitrary portions and adding them, such as dividing into two or three portions and then adding them intermittently.

In addition, examples of the addition of one after another in the present invention include a method that involves: beforehand charging a portion of an alkylene oxided as an initial charging amount; and thereafter continuously and/or intermittently adding the remainder in order to start a reaction. In this case, the initial charging amount of the alkylene oxide is favorably in the range of 0.1 to 30 weight %, more favorably 0.5 to 20 weight %, still more favorably 1 to 10 weight %.

When the continuous addition is carried out, the addition may proceed until the end of the addition while the addition speed is kept constant, or may proceed with changing the speed at least once in mid course, or may proceed with continuously varying the speed itself arbitrarily. The mode for the continuous addition is not especially limited, but the mode of changing the speed once in mid course and decreasing the speed before to after changing the speed is more favorable among them.

As to the addition of the raw (meth)acrylic acid and the raw alkylene oxide to the reactor, they may be added from separate addition lines respectively. They are beforehand blended in a pipe, a line mixer, or a mixing tank before they are added to the reactor, and thereafter they may be added. In addition, the raw materials may be added at an ordinary temperature, or may be added after they are beforehand heated to a desired reaction temperature. In addition, when the liquid obtained from the outlet of the reactor is circulated to the inlet of the reactor or the unreacted (meth)acrylic acid and the unreacted alkylene oxide are recovered and recycled, these liquids may be added to the reactor after they are blended with the raw (meth)acrylic acid and the raw alkylene oxide. However, when the (meth)acrylic acid and the alkylene oxide are added from separate addition lines, the molar ratio of the (meth)acrylic acid in the reaction liquid is excess in the neighborhood where the (meth)acrylic acid is added. Therefore, the respective raw materials are beforehand blended in such as a pipe before they are added to the reactor, and then they may be added thereto.

The catalyst for the reaction usable in the present invention is not especially limited, but favorable examples thereof include at least one member selected from the group consisting of: chromium compounds such as chromium chloride, chromium acetylacetonate, chromium formate, chromium acetate, chromium acrylate, chromium methacrylate, sodium bichromate, and chromium dibutyldithiocarbamate; iron compounds such as iron powder, ferric chloride, iron formate, iron acetate, iron acrylate, and iron methacrylate; and amines such as trialkylamines, cyclic amines (e.g. pyridine) and their quaternary ammonium salts, and resins having a basic functional group (e.g. tertiary amino groups, quaternary ammonium salts, and pyridinium groups).

The amount of the catalyst is not especially limited, but, when the catalyst is a homogeneous catalyst, the catalyst is favorably used in the range of 0.05 to 10 weight %, more favorably 0.1 to 3 weight % of the raw (meth)acrylic acid. Furthermore, when the homogeneous catalyst is used, the catalyst is generally charged in a reactor beforehand. However, the catalyst is not especially limited and can be charged in a reactor after dissolving with the raw (meth)acrylic acid in a dissolving tank different from the reactor. On the other hand, when the catalyst is a heterogeneous catalyst and the reaction is carried out in a batch manner, the catalyst is favorably used in the range of 5 to 80 weight %, more favorably 10 to 70 weight % of the raw (meth)acrylic acid.

In addition, polymerization inhibitors may be added to the reaction liquid if necessary. The polymerization inhibitor is not especially limited, and can be used if it is generally and industrially used. Examples thereof include: phenol compounds such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, and hydroquinone monomethyl ether; 1,4-phenylenediamines such as N-isopropyl-N'-phenyl-1,4-phenylenediamine, N-(1,3-dimethylbutyl)-N'-phenyl-1,4-phenylenediamine, N-(1-methylheptyl)-N'-phenyl-1,4-phenylenediamine, N,N'-diphenyl-1,4-phenylenediamine, and N,N'-di-2-naphthyl-1,4-phenylenediamine; amine compounds such as thiodiphenylamine and phenothiazine; copper dialkyldithiocarbamates such as copper dibutyldithiocarbamate, copper diethyldithiocarbamate, and copper dimethyldithiocarbamate; and N-oxyl compounds such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, and 2,2,6,6-tetramethyl-4-benzoyloxypiperidine-1-oxyl. These polymerization inhibitors may be used either alone respectively or in combinations with each other.

The amount of the polymerization inhibitor as added is favorably in the range of 0.0001 to 1 weight %, more favorably 0.001 to 0.5 weight % relative to the raw (meth)acrylic acid.

In the production process for a hydroxyalkyl(meth)acrylate according to the present invention, the alkylene oxide is added one after another, namely, continuously and/or intermittently, and is allowed to react with the (meth)acrylic acid.

The amount of the alkylene oxide as supplied (the total amount of the alkylene oxide as supplied) is favorably in the range of 1.0 to 10 mol, more favorably 1.0 to 5.0 mol, more favorably 1.0 to 3.0 mol, still more favorably 1.0 to 2.0 mol, per 1 mol of the (meth)acrylic acid. In the case where the amount of the alkylene oxide as supplied is less than the amount equimolar with the (meth)acrylic acid, there are disadvantages in that the reaction cannot proceed and the characteristic process according to the present invention cannot be carried out. In addition, in the case where the amount of the alkylene oxide as supplied is more than 10 mol, there are disadvantages in economy because of requiring a recovery step.

The production process, according to the present invention, is characterized by varying a supplying speed of the alkylene oxide so as to adjust to specific conditions during a supplying period.

One of the specific conditions is that: when the time from the start of adding the alkylene oxide till the end of supplying the entirety of the alkylene oxide is defined as T (hour), the amount of more than 50% of the entirety of the alkylene oxide is supplied before T/2 (hour) has passed since the start of adding the alkylene oxide.

Before T/2 (hour) has passed since the start of adding the alkylene oxide, the alkylene oxide is favorably supplied in an amount of more than 50% and not more than 95% of the entirety, more favorably in the range of 60 to 90%, still more favorably 65 to 85%, particularly favorably 70 to 80%.

The time T (hour) from the start of adding the alkylene oxide till the end of supplying the entirety of the alkylene oxide is fitly varied according to various reaction conditions, but it is favorably in the range of 3 to 6 hours.

The alkylene oxide is supplied so as to satisfy this specific condition. Therefore, the amount of the alkylene oxide as supplied at the first half portion of the reaction is more than that as supplied at the latter half portion of the reaction. This supplying mode causes shortening the supplying time of the alkylene oxide and improving productivity in comparison with the case that the alkylene oxide is conventionally supplied with a constant speed. Furthermore, the side-formation of impurities such as a diester or a monoester can be suppressed wherein the impurities have a bad influence on product quality. In addition, the reaction rate is increased and the concentration of the residual alkylene oxide at the end of the supply can be suppressed low. Therefore, the problem of high danger of explosion can also be avoided.

Another specific condition is that: when the total amount of the alkylene oxide as supplied and the time from the start of adding the alkylene oxide till the end of supplying the entirety of the alkylene oxide are defined as W (mol) and T (hour) respectively, the supply of the alkylene oxide is started at a supplying speed V0 (mol/hour) that is faster than the average supplying speed V (=W/T) (mol/hour), and thereafter the supplying speed of the alkylene oxide is decreased at least once, and then the supply of the entirety of the alkylene oxide is completed for T (hour) from the start of adding the alkylene oxide.

The time T (hour) from the start of adding the alkylene oxide till the end of supplying the entirety of the alkylene oxide is fitly varied according to various reaction conditions, but it is favorably in the range of 3 to 6 hours.

The supplying speed V0 (mol/hour) of the alkylene oxide is favorably at least 1.1 times faster, more favorably at least 1.3 times faster, still more favorably at least 1.7 times faster, particularly favorably at least 2 times faster, than the average supplying speed V (=W/T) (mol/hour).

In the specific condition, the supplying speed of the alkylene oxide is decreased at least once after the beginning of supplying the alkylene oxide, and then the supply of the entirety of the alkylene oxide is completed for T (hour) from the start of adding the alkylene oxide. The procedure of decreasing the supplying speed of the alkylene oxide may be carried out again and again if the procedure is carried out at least once, or the supplying speed may be decreased stepwise or non-stepwise (continuously), or may be decreased in combinations with each other. It is favorable that the supply of the entirety of the alkylene oxide can be finally completed for T (hour) from the start of adding the alkylene oxide.

The alkylene oxide is supplied so as to satisfy this specific condition. Therefore, the amount of the alkylene oxide as supplied at the first half portion of the reaction is more than that as supplied at the latter half portion of the reaction. This supplying mode causes shortening the supplying time of the alkylene oxide and improving productivity in comparison with the case that the alkylene oxide is conventionally supplied with a constant speed. Furthermore, the side-formation of impurities such as a diester or a monoester can be suppressed wherein the impurities have a bad influence on product quality. In addition, the reaction rate is increased and the concentration of the residual alkylene oxide at the end of the supply can be suppressed low. Therefore, the problem of high danger of explosion can also be avoided.

The means of evaluating the above danger of explosion is not especially limited, but examples thereof include an evaluation method from composition of a gas-phase portion in the reaction system at the end of supplying the alkylene oxide, more particularly, an evaluation method from the concentration of alkylene oxide and the concentration of oxygen. Then, the danger of explosion, which is evaluated from the concentration of the alkylene oxide and the concentration of the oxygen, is dependent upon environmental conditions, such as temperature, pressure, and space volume in the reaction system. For example, when the reaction is carried out under general environmental conditions, the danger of explosion can also be avoided if the above concentration of the oxygen is in the range of 3 to 4 volume % and the above concentration of the alkylene oxide is smaller than 25 volume %, favorably smaller than 20 volume %, more favorably smaller than 15 volume %.

In the production process for a hydroxyalkyl(meth) acrylate, which is characterized by varying a supplying speed of the alkylene oxide so as to adjust to specific conditions during a supplying period, the temperature of the reaction between the (meth)acrylic acid and the alkylene oxide is favorably in the range of 40 to 100° C., more favorably 45 to 90° C., still more favorably 45 to 80° C., particularly favorably 50 to 80° C.

In the case where the above temperature range is lower than 40° C., the reaction rate is extremely decreased, and the gas concentration of the unreacted alkylene oxide is increased in the gas phase, and the explosion may be caused. Therefore, it is necessary to dilute the gas-phase portion with an inert gas and to lower the gas concentration of the alkylene oxide in the gas phase so that safety can be ensured. In the case, there are disadvantages in economy because it is necessary to increase the planned pressure of the reactor. In addition, there is also a method that involves decreasing the addition speed of the alkylene oxide and lowering the concentration of the unreacted alkylene oxide, but the reaction time is long and the productivity is lowered.

In addition, in the case where the above temperature range is higher than 100° C., there are disadvantages in that it is difficult to suppress the formation of the diester or the monoester.

It is important to control the reaction temperature in yet another production process according to the present invention, namely, the method that involves controlling the reaction temperature in the range of a low temperature while the reaction conversion of the (meth)acrylic acid is low, and elevating the reaction temperature when the reaction conversion of the (meth)acrylic acid is high to a certain extent. That is to say, the production process comprises:

(1) the alkylene-oxide supplying step of mildly carrying out the reaction with maintaining a reaction temperature during the supply of the alkylene oxide in the range of 40 to 100° C.; thereafter (2) the step of heating to a temperature higher than the reaction temperature at the end of the alkylene-oxide supplying step by at least 3° C.; and thereafter (3) the aging step of continuing the reaction at a reaction temperature not lower than the temperature after the heating step; and wherein (4) the heating step is started when the reaction conversion of the (meth)acrylic acid is not less than 50%.

In the production process according to the present invention, the reaction is mildly carried out in the alkylene-oxide supplying step while the reaction temperature is maintained in the temperature range of 40 to 100° C. Therefore, the reaction can proceed while the formation of the diester or the monoester is suppressed to the maximum limit. It is found that the formation amount of the diester or the monoester highly depends upon the temperature in a component state of the reaction liquid within this period. Therefore, it is important to mildly carry out the reaction while the reaction temperature is controlled within a low temperature range, in order to suppress the formation of the diester or the monoester. However, if the temperature is too low, the reaction rate is extremely decreased. Accordingly, as a result of consideration, it was found that the temperature range of 40 to 100° C., which is determined in the present invention, is a temperature range in which the suppress of the formation amount of the diester or the monoester is compatible with the suppress of decreasing the reaction rate. This reaction temperature is favorably in the range of 40 to 100° C., more favorably 45 to 90° C., still more favorably 45 to 80° C., particularly favorably 50 to 80° C.

In the case where the above temperature range is lower than 40° C., the reaction rate is extremely decreased, the gas concentration of the unreacted alkylene oxide is increased in gas phase, and then the explosion may be caused. Therefore, the gas phase is diluted with inert gas to ensure safety, and it is necessary to decrease the gas concentration of the alkylene oxide in the gas phase. In the case, there are disadvantages in economy because it is necessary to raise the planned pressure of reactor. In addition, there is also a method that involves decreasing the addition rate of the alkylene oxide and lowering the concentration of the unreacted alkylene oxide. However, the reaction time is lengthened and the productivity is lowered.

In addition, in the case where the above temperature range is higher than 100° C., there are disadvantages in that it is difficult to suppress the formation of the diester or the monoester.

In addition, it is generally known that the (meth)acrylic acid easily produces its dimmer in the presence of no catalyst at high temperature. However, the formation of the (meth)acrylic acid dimmer as produced in the reaction can be suppressed in the present invention because the reaction temperature, while the reaction conversion of the (meth) acrylic acid is low, namely, the concentration of the unreacted (meth)acrylic acid is high, is lower than the conventional reaction temperature. In addition, if the reaction temperature is lowered in the above way, the esterification caused by the (meth)acrylic acid dimmer and the alkylene oxide can also be suppressed, and the reaction yield can be improved.

Furthermore, when the time of the alkylene-oxide supplying step is defined as T (hour), as is mentioned in the above way, the favorable mode is that the amount of more than 50% of the entirety of the alkylene oxide is supplied before T/2 (hour) has passed since the start of adding the alkylene oxide.

In addition, when the total amount of the alkylene oxide as supplied and the time of the alkylene oxide-supplying step are defined as W (mol) and T (hour) respectively, as is mentioned in the above way, the favorable mode is that: the supply of the alkylene oxide is started at a supplying speed V0 (mol/hour) that is faster than the average supplying speed V (=W/T) (mol/hour), and thereafter the supplying speed of the alkylene oxide is decreased at least once, and then the supply of the entirety of the alkylene oxide is completed for T (hour) from the start of adding the alkylene oxide.

Furthermore, in the production process according to the present invention, while the formation of the diester or the monoester is suppressed to the maximum limit, the reaction can proceed by: when the reaction conversion of the (meth)acrylic acid is not less than 50% in the reaction liquid, heating to a temperature higher than the reaction temperature at the end of the alkylene-oxide supplying step by at least 3° C.; and thereafter carrying out the aging step of continuing the reaction at a reaction temperature not lower than the temperature after the heating step. The formation amount of the diester or the monoester lowly depends upon the temperature in the component state of the reaction liquid within this period when "the reaction conversion of the (meth)acrylic acid is not less than 50% in the reaction liquid". Therefore, even if the reaction temperature is controlled within a higher temperature range, the formation of the diester or the monoester can be suppressed and the reaction rate is improved. However, if the reaction temperature is too high, not only the formation of the diester or the monoester cannot be suppressed but also the reaction liquid is partially polymerized and the productivity is lowered. Accordingly, as a result of consideration, it was found that: the temperature range, in which the suppress of forming the diester or the monoester is compatible with the rapid reaction rate, is obtained if the following conditions are satisfied: the heating step is started "when the reaction conversion of the (meth)acrylic acid is not less than 50%", as is determined in the present invention; and "the reaction temperature of the alkylene-oxide supplying step before the heating step is maintained in the range of 40 to 100° C." as mentioned above.

The above heating temperature is a temperature higher than the reaction temperature at the end of the alkylene-oxide supplying step by at least 3° C., favorably by 3 to 50° C., more favorably by 5 to 50° C., still more favorably by 5 to 45° C., particularly favorably by 5 to 40° C. In addition, the reaction time of the aging step, namely, after the heating step, is favorably not shorter than 0.5 hour, more favorably in the range of 0.5 to 10 hours, still more favorably 0.5 to 5 hours, particularly favorably 1 to 5 hours.

In addition, the method for raising the reaction temperature is not especially limited in a batch reaction manner if the heating is started when the reaction conversion of the (meth)acrylic acid is not less than 50%, but the heating step may be carried out while or after being supplied the alkylene oxide, or while being aged. In addition, the heating step may be carried out stepwise once or at least twice when the occasion demands.

In the present invention, the polymerization of the hydroxyalkyl(meth)acrylate can be suppressed in the reaction because the formation of the diester that is a polymerization promoting substance of the aimed hydroxyalkyl (meth)acrylate is usually suppressed more than that in the past. The productivity can also be improved because clogs caused by the polymerization in a reactor and pipe disappears.

In the production process according to the present invention, diester-forming inhibitors may be divided into two or more portions and then added in the production steps including: the reaction and distillation, the reaction, or the aging and distillation. Examples of the diester-forming inhibitors include: carboxylic acids and their anhydrides, such as oxalic acid, oxalic anhydride, malonic acid, succinic acid, succinic anhydride, fumaric acid, maleic acid, maleic anhydride, salicylic acid, octanic acid, adipic acid, sebasic acid, tetradecanedicarboxylic acid, 1,2,4-butanetricarboxylic acid, 1,3,6-hexanetricarboxylic acid, 1,2,3,4-butanetetracarboxylic acid, 1,2,3,4-pentanetetracarboxylic acid, 1,6,7,12-dodecanetetracarboxylic acid, benzoic acid, o-toluic acid, m-toluic acid, p-toluic acid, phthalic acid, phthalic anhydride, isophthalic acid, terephthalic acid, 2,6-naphthalenedicarboxylic acid, pyromellitic acid, pyromellitic anhydride, trimellitic acid, trimellitic anhydride, 1,2,4-benzenetricarboxylic acid, 1,4,5,8-naphthalenetetracarboxylic acid, 1,3,5,7-naphthalenetrtracraboxylic acid, and poly(acrylic acid); polyhydric alcohols, such as glycerin, dietheylene glycol, trimethylolpropane, cresol, 1,2,6-hexanetriol, pentaerythritol, dipentaerythritol, 2,3,4,5-tetrahydroxyhexane, xylitol, mannitol, catechol, resorcin, 2,6-dihydroxytoluene, tert-butylcatechol, pyrogallol, 2,4-bis (hydroxymethyl)phenol, 1,2,4-trihydroxybenzene, 1,3,5-trihydroxybenzene, 2,4,6-tris(hydroxymethyl)phenol, and 1,2,4,5-tetrahydroxybenzene; and metal chelating agents, such as ethylenediaminetetraacetic acid, ethylenediaminetetrapropionic acid, nitrilotriacetic acid, iminodiacetic acid, 1,2-diaminocyclohexanetetraacetic acid, acetylacetone, cupferron, oxine, bendizidine, diethyl dithiocarbamate. One or more compounds, which are selected from the above group, are favorably used.

In the production process according to the present invention, the reaction may be carried out in a solvent for the purpose, such as mildly carrying out the reaction. As to the solvent, the following conventional solvents can be used: toluene, xylene, heptane, and octane.

In the production process according to the present invention, the pressure in the reaction system depends upon the kinds of raw materials or the mixing ratio, but the reaction is generally carried out under compressed pressure.

EFFECTS AND ADVANTAGES OF THE INVENTION

According to the present invention, the supplying time of the alkylene oxide can be shortened and the productivity is improved. Furthermore, the side-formation of impurities (for example, the diester or the monoester) that have a bad influence on product quality can be suppressed. In addition, in comparison with the case that the alkylene oxide is conventionally supplied with a constant speed, the concentration of the residual alkylene oxide at the end of the supply can be suppressed low, and the problem of high danger of explosion can also be avoided.

DETAILED DESCRIPTION OF THE PREFERRED EMBODIMENTS

Hereinafter, the present invention is more specifically illustrated by the following examples and comparative examples. However, the present invention is not limited thereto.

EXAMPLE 1

SUS-316 made autoclave having a capacity of 1.5 L equipped with a stirrer was charged with 658 g of acrylic acid, 2.62 g of chromium acetate as a catalyst, and 1.44 g of hydroquinone monomethyl ether as a polymerization inhibitor, and the inner temperature was raised to 50° C. Thereafter, the inside of the autoclave was replaced with nitrogen, and the concentration of oxygen and the inner pressure were adjusted to 4 volume % and 0.1 MPa, respectively.

Thereafter, 287 g of ethylene oxide was supplied into the autoclave over a period of 60 minutes. Thereafter, the supplying speed was changed, and 143 g of the ethylene oxide was supplied over a period of 120 minutes. The temperature was maintained at 50° C. in the mean while.

As to the composition of the reaction liquid at the end of supplying the ethylene oxide, the amount of the acrylic acid and the amount of the ethylene oxide were 19.5 weight % and 12.3 weight % respectively, and the reaction conversion of the acrylic acid was 68%. In addition, the concentration of the ethylene oxide in a gas-phase portion of the autoclave was then 23 volume %, and the concentration of the oxygen was 3.5 volume %.

After the end of supplying the ethylene oxide, the resultant mixture was heated to 70° C., and the reaction was continued until the amount of the unreacted acrylic acid reached not more than 0.10 weight %. The reaction was continued for 3 hours, and then the amount of the unreacted acrylic acid reached 0.09 weight %. Accordingly, the resultant reaction liquid was cooled. The concentration of hydroxyethyl acrylate in the resultant reaction liquid was 91.4 weight %, and the concentration of ethylene glycol diacrylate was 0.18 weight %, and the concentration of diethylene glycol monoacrylate was 7.4 weight %.

COMPARATIVE EXAMPLE 1

The same procedure as of Example 1 was carried out except that 430 g of the ethylene oxide was supplied at a constant speed over a period of 240 minutes.

As to the composition of the reaction liquid at the end of supplying the ethylene oxide, the amount of the acrylic acid and the amount of the ethylene oxide were 20.3 weight % and 13.9 weight % respectively, and the reaction conversion of the acrylic acid was 66%. In addition, the concentration of the ethylene oxide in a gas-phase portion of the autoclave was then 25 volume %, and the concentration of the oxygen was 3.5 volume %. These concentrations meant that the gas-phase portion was outside of explosive range in the same way as of Example 1.

After the end of supplying the ethylene oxide, the resultant mixture was heated to 70° C., and the reaction was continued for 3.5 hours. Then the amount of the unreacted acrylic acid reached 0.09 weight %. Accordingly, the resultant reaction liquid was cooled. The concentration of hydroxyethyl acrylate in the resultant reaction liquid was 90.2 weight %, and the concentration of ethylene glycol diacrylate was 0.24 weight %, and the concentration of diethylene glycol monoacrylate was 8.2 weight %.

In Comparative Example 1, the concentration of the ethylene oxide in a gas-phase portion of the autoclave at the end of supplying the ethylene oxide was nearly equal to that of Example 1, and both did not have danger of explosion. However, in comparison with Example 1, the formation amount of the diester and the monoester as by-products was increased, and besides the reaction time lengthened for 1.5 hours and the productivity was lowered.

COMPARATIVE EXAMPLE 2

The same procedure as of Example 1 was carried out except that 430 g of the ethylene oxide was supplied at a constant speed over a period of 180 minutes.

As to the composition of the reaction liquid at the end of supplying the ethylene oxide, the amount of the acrylic acid and the amount of the ethylene oxide were 25.3 weight % and 16.5 weight % respectively, and the reaction conversion of the acrylic acid was 58%. In addition, the concentration of the ethylene oxide in a gas-phase portion of the autoclave was then 30 volume %, and the concentration of the oxygen was 3.5 volume %. These concentrations meant that the gas-phase portion was within explosive range and the danger of explosion was caused. Therefore, the reaction was continued after it was confirmed that there was no ignition source near here.

After the end of supplying the ethylene oxide, the resultant mixture was heated to 70° C., and the reaction was continued for 3 hours. Then, the amount of the unreacted acrylic acid reached 0.08 weight %. Accordingly, the resultant reaction liquid was cooled. The concentration of hydroxyethyl acrylate in the resultant reaction liquid was 91.2 weight %, and the concentration of ethylene glycol diacrylate was 0.20 weight %, and the concentration of diethylene glycol monoacrylate was 7.5 weight %.

In Comparative Example 2, the formation amount of the diester and the monoester as by-products was nearly equal to that of Example 1. However, the concentration of the ethylene oxide in a gas-phase portion of the autoclave at the end of supplying the ethylene oxide was higher than that of Example 1, and the danger of explosion was increased.

EXAMPLE 2

SUS-316 made autoclave having a capacity of 1.5 L equipped with a stirrer was charged with 746 g of methacrylic acid, 2.62 g of chromium acetate as a catalyst, and 2.24 g of phenothiazine as a polymerization inhibitor, and the inner temperature was raised to 60° C. Thereafter, the inside of the autoclave was replaced with nitrogen, and the concentration of oxygen and the inner pressure were adjusted to 4 volume % and 0.1 MPa, respectively.

Thereafter, 272 g of ethylene oxide was supplied into the autoclave over a period of 90 minutes. Thereafter, the supplying speed was changed, and 117 g of the ethylene oxide was supplied over a period of 60 minutes. The temperature was maintained at 60° C. in the mean while.

As to the composition of the reaction liquid at the end of supplying the ethylene oxide, the amount of the methacrylic acid and the amount of the ethylene oxide were 26.8 weight % and 12.8 weight % respectively, and the reaction conversion of the methacrylic acid was 59%. In addition, the concentration of the ethylene oxide in a gas-phase portion of the autoclave was then 24 volume %, and the concentration of the oxygen was 3.8 volume %.

After the end of supplying the ethylene oxide, the resultant mixture was heated to 75° C., and the reaction was continued until the amount of the unreacted methacrylic acid reached not more than 0.10 weight %. The reaction was continued for 3 hours, and then the amount of the unreacted methacrylic acid reached 0.09 weight %. Accordingly, the resultant reaction liquid was cooled. The concentration of hydroxyethyl methacrylate in the resultant reaction liquid was 95.7 weight %, and the concentration of ethylene glycol dimethacrylate was 0.06 weight %, and the concentration of diethylene glycol monomethacrylate was 3.5 weight %.

COMPARATIVE EXAMPLE 3

The same procedure as of Example 2 was carried out except that: the supplying speed was changed after 58 g of the ethylene oxide was supplied over a period of 38 minutes; and then 331 g of the ethylene oxide was supplied over a period of 112 minutes.

As to the composition of the reaction liquid at the end of supplying the ethylene oxide, the amount of the methacrylic acid and the amount of the ethylene oxide were 32.2 weight % and 15.1 weight % respectively, and the reaction conversion of the methacrylic acid was 51%. In addition, the concentration of the ethylene oxide in a gas-phase portion of the autoclave was then 28 volume %, and the concentration of the oxygen was 3.8 volume %. This gas composition meant that the gas-phase portion was within explosive range and the danger of explosion was caused. Therefore, the reaction was continued after it was confirmed that there was no ignition source near here.

After the end of supplying the ethylene oxide, the resultant mixture was heated to 75° C., and the reaction was continued for 3.5 hours. Then the amount of the unreacted methacrylic acid reached 0.08 weight %. Accordingly, the resultant reaction liquid was cooled. The concentration of hydroxyethyl methacrylate in the resultant reaction liquid was 94.6 weight %, and the concentration of ethylene glycol dimethacrylate was 0.15 weight %, and the concentration of diethylene glycol monomethacrylate was 4.0 weight %. Therefore, the formation amount of the by-products was more than that of Example 2.

In Comparative Example 3, the concentration of the ethylene oxide in a gas-phase portion of the autoclave at the end of supplying the ethylene oxide was higher than that of Example 2, and the danger of explosion was increased. In addition, in comparison with Example 2, the formation amount of the diester or the monoester as by-products was increased, and besides the reaction time lengthened for 0.5 hour and the productivity was lowered.

EXAMPLE 3

SUS-316 made autoclave having a capacity of 1.5 L equipped with a stirrer was charged with 663 g of acrylic acid, 3.32 g of chromium acetate as a catalyst, and 1.03 g of hydroquinone monomethyl ether as a polymerization inhibitor. Thereafter, 55 g of propylene oxide was added into the autoclave with a metering pump. Thereafter, the inner temperature was raised to 55° C., and the inside of the autoclave was replaced with nitrogen while the temperature was raised, and the concentration of oxygen and the inner pressure were adjusted to 3.5 volume % and 0.1 MPa, respectively.

When the reaction temperature reached 55° C., the addition of the propylene oxide was started, and 330 g of the propylene oxide was supplied over a period of 90 minutes. Thereafter, the supplying speed was changed, and 202 g of the propylene oxide was supplied over a period of 150 minutes. The reaction temperature was maintained at 55° C. in the mean while.

As to the composition of the reaction liquid at the end of supplying the propylene oxide, the amount of the acrylic acid and the amount of the propylene oxide were 20.2 weight % and 15.4 weight % respectively, and the reaction conversion of the acrylic acid was 62%. In addition, the concentration of the propylene oxide in a gas-phase portion of the autoclave was then 15 volume %, and the concentration of the oxygen was 3.2 volume %.

After the end of supplying the propylene oxide, the resultant mixture was heated to 70° C., and the reaction was continued until the amount of the unreacted acrylic acid reached not more than 0.1 weight %. The reaction was continued for 2.5 hours, and then the amount of the unreacted acrylic acid reached 0.09 weight %. Accordingly, the resultant reaction liquid was cooled. The concentration of hydroxypropyl acrylate in the resultant reaction liquid was 94.3 weight %, and the concentration of propylene glycol diacrylate was 0.15 weight and the concentration of dipropylene glycol monoacrylate was 4.2 weight %.

COMPARATIVE EXAMPLE 4

The same procedure as of Example 3 was carried out except that: the addition of the propylene oxide was not started when the reaction temperature reached 55° C., but it was started when the reaction temperature was maintained at 55° C. for another hour after the reaction temperature reached 55° C.

As to the composition of the reaction liquid at the end of supplying the propylene oxide, the amount of the acrylic acid and the amount of the propylene oxide were 18.5 weight % and 13.7 weight % respectively, and the reaction conversion of the acrylic acid was 65%. In addition, the concentration of the propylene oxide in a gas-phase portion of the autoclave was then 14 volume %, and the concentration of the oxygen was 3.3 volume %.

After the end of supplying the propylene oxide, the resultant mixture was heated to 70° C., and the reaction was continued for 3 hours. Then the amount of the unreacted acrylic acid reached 0.09 weight %. Accordingly, the resultant reaction liquid was cooled. The concentration of hydroxypropyl acrylate in the resultant reaction liquid was 91.6 weight %, and the concentration of propylene glycol diacrylate was 0.27 weight %, and the concentration of dipropylene glycol monoacrylate was 7.6 weight %.

In Comparative Example 4, the concentration of the propylene oxide in a gas-phase portion of the autoclave at the end of supplying the propylene oxide was nearly equal to that of Example 3, and either of them did not have danger of explosion. However, in comparison with Example 3, the formation amount of the diester and the monoester as by-products was increased, and besides the reaction time lengthened and the productivity was lowered in proportion to the reaction passage.

COMPARATIVE EXAMPLE 5

The same procedure as of Example 1 was carried out except that the reaction temperature was maintained at a constant temperature of 50° C. after the end of supplying the ethylene oxide.

The reaction was continued for 7.0 hours after the end of supplying the ethylene oxide, and then the amount of the unreacted acrylic acid reached 0.10 weight %. Accordingly, the resultant reaction liquid was cooled. The concentration of hydroxyethyl acrylate in the resultant reaction liquid was 90.6 weight %, and the concentration of ethylene glycol diacrylate was 0.20 weight %, and the concentration of diethylene glycol monoacrylate was 7.7 weight %. Therefore, the formation amount was equal to that of Example 1. However, the aging time after the end of supplying the ethylene oxide was at least twice as long as that of Example 1, and the productivity was lowered.

EXAMPLE 4

SUS-316 made autoclave having a capacity of 1.5 L equipped with a stirrer was charged with 615 g of methacrylic acid, 1.23 of chromium acetate as a catalyst, and 0.62 g of phenothiazine as a polymerization inhibitor and the inner temperature was raised to 80° C. Thereafter, the inside of the autoclave was replaced with nitrogen, and the concentration of oxygen and the inner pressure were adjusted to 3 volume % and 0.1 MPa, respectively.

Thereafter, 290 g of propylene oxide was supplied into the autoclave over a period of 240 minutes. The temperature was maintained at 80° C. in the mean while.

As to the composition of the reaction liquid at the end of supplying the propylene oxide, the amount of the methacrylic acid and the amount of the propylene oxide were 12.2 weight % and 9.7 weight %, respectively, and the reaction conversion of the methacrylic acid was 82%. In addition, the concentration of the propylene oxide in a gas-phase portion of the autoclave was then 20 volume %, and the concentration of the oxygen was 2.6 volume %.

After the end of supplying the propylene oxide, the resultant mixture was heated to 90° C., and the reaction was continued until the amount of the unreacted methacrylic acid reached not more than 0.10 weight %. The reaction was continued for 3 hours, and then the amount of the unreacted methacrylic acid reached 0.08 weight %. Accordingly, the resultant reaction liquid was cooled. The concentration of hydroxypropyl methacrylate in the resultant reaction liquid was 96.7 weight and the concentration of propylene glycol dimethacrylate was 0.08 weight %, and the concentration of dipropylene glycol monomethacrylate was 2.4 weight %.

COMPARATIVE EXAMPLE 6

The same procedure as of Example 1 was carried out except that the reaction temperature was maintained at a constant temperature of 50° C. for two hours from the beginning of supplying the ethylene oxide, and then the reaction temperature was raised to 70° C. The reaction conversion of the acrylic acid was 45% after two hours from the beginning of supplying the ethylene oxide.

The reaction was continued for 2.0 hours after the end of supplying the ethylene oxide, and then the amount of the unreacted acrylic acid reached 0.09 weight %. Accordingly, the resultant reaction liquid was cooled. The aging time after the end of supplying the ethylene oxide was equal to that of Example 1. The concentration of hydroxyethyl acrylate in the resultant reaction liquid was 89.4 weight %, and the concentration of ethylene glycol diacrylate and the concentration of diethylene glycol monoacrylate were increased to 0.30 weight % and 8.8 weight %, respectively.

COMPARATIVE EXAMPLE 7

The same procedure as of Example 4 was carried out except that the reaction temperature was maintained at a constant temperature of 80° C. after the end of supplying the propylene oxide. The reaction was continued for 6.5 hours after the end of supplying the propylene oxide, and then the amount of the unreacted methacrylic acid reached 0.10 weight %. Accordingly, the resultant reaction liquid was cooled. The concentration of hydroxypropyl methacrylate in the resultant reaction liquid was 96.8 weight %, and the concentration of propylene glycol dimethacrylate was 0.08 weight %, and the concentration of dipropylene glycol monomethacrylate was 2.5 weight %. The formation amount was equal to that of Example 4. However, the aging time after the end of supplying the propylene oxide was at least twice as long as that of Example 4, and the productivity was lowered.

COMPARATIVE EXAMPLE 8

The same procedure as of Example 4 was carried out except that the reaction temperature was maintained at a constant temperature of 90° C. during the supply of the propylene oxide. The reaction conversion of the methacrylic acid after the end of supplying the propylene oxide was 90%. The reaction was continued for 2.5 hours after the end of supplying the propylene oxide, and then the amount of the unreacted methacrylic acid reached 0.10 weight %. Accordingly, the resultant reaction liquid was cooled. The aging time after the end of supplying the propylene oxide was equal to that of Example 4. The concentration of hydroxypropyl methacrylate in the resultant reaction liquid was 95.6 weight %, and the concentration of propylene glycol dimethacrylate and the concentration of dipropylene glycol monomethacrylate were increased to 0.15 weight % and 3.5 weight %, respectively.

COMPARATIVE EXAMPLE 9

The same procedure as of Example 4 was carried out except that the reaction temperature was maintained at a constant temperature of 80° C. for two hours from the beginning of supplying the propylene oxide, and then the reaction temperature was raised to 90° C. The reaction conversion of the methacrylic acid was 42% after two hours from the beginning of supplying the propylene oxide. The reaction was continued for 2.9 hours after the end of supplying the propylene oxide, and then the amount of the unreacted methacrylic acid reached 0.10 weight %. Accordingly, the resultant reaction liquid was cooled. The aging time after the end of supplying the propylene oxide was equal to that of Example 4. However, the temperature was raised when the reaction conversion of the methacrylic acid was less than 50%. Therefore, the concentration of hydroxypropyl methacrylate in the resultant reaction liquid was 96.1 weight %, and the concentration of propylene glycol dimethacrylate and the concentration of dipropylene glycol monomethacrylate were increased to 0.14 weight % and 3.1 weight %, respectively.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a hydroxyalkyl(meth)acrylate, which comprises the step of carrying out a reaction between (meth)acrylic acid and an alkylene oxide in the presence of a catalyst in order to produce the hydroxyalkyl(meth) acrylate, wherein:

when the time from the start of adding the alkylene oxide till the end of supplying the entirety of the alkylene oxide is defined as T (hour), the amount of more than 50% of the entirety of the alkylene oxide is supplied before T/2 (hour) has passed since the start of adding the alkylene oxide.

2. A production process for a hydroxyalkyl(meth)acrylate, which comprises the step of carrying out a reaction between (meth)acrylic acid and an alkylene oxide in the presence of a catalyst in order to produce the hydroxyalkyl(meth)acrylate, wherein:

when the total amount of the alkylene oxide as supplied and the time from the start of adding the alkylene oxide till the end of supplying the entirety of the alkylene oxide are defined as W (mol) and T (hour) respectively, the supply of the alkylene oxide is started at a supplying speed V0 (mol/hour) that is faster than the average supplying speed V (=W/T) (mol/hour), and thereafter the supplying speed of the alkylene oxide is decreased at least once, and then the supply of the entirety of the alkylene oxide is completed for T (hour) from the start of adding the alkylene oxide.

3. A production process for a hydroxyalkyl(meth)acrylate, which comprises the step of carrying out a reaction between (meth)acrylic acid and an alkylene oxide in the presence of a catalyst in order to produce the hydroxyalkyl(meth)acrylate, with the production process further comprising: the alkylene-oxide supplying step of mildly carrying out the reaction with maintaining a reaction temperature during the supply of the alkylene oxide in the range of 40 to 100° C.; thereafter the step of heating to a temperature higher than the reaction temperature at the end of the alkylene-oxide supplying step by at least 3° C.; thereafter the aging step of continuing the reaction at a reaction temperature not lower than the temperature after the heating step, and wherein the heating step is started when the reaction conversion of the (meth)acrylic acid is not less than 50%.

4. A production process for a hydroxyalkyl(meth)acrylate according to claim 3, wherein:

when the time of the alkylene-oxide supplying step is defined as T (hour), the amount of more than 50% of the entirety of the alkylene oxide is supplied before T/2 (hour) has passed since the start of adding the alkylene oxide.

5. A production process for a hydroxyalkyl(meth)acrylate according to claim 3, wherein:

when the total amount of the alkylene oxide as supplied and the time of the alkylene oxide-supplying step are defined as W (mol) and T (hour) respectively, the supply of the alkylene oxide is started at a supplying speed V0 (mol/hour) that is faster than the average supplying speed V (=W/T) (mol/hour), and thereafter the supplying speed of the alkylene oxide is decreased at least once, and then the supply of the entirety of the alkylene oxide is completed for T (hour) from the start of adding the alkylene oxide.

* * * * *

UNITED STATES PATENT AND TRADEMARK OFFICE
CERTIFICATE OF CORRECTION

PATENT NO.    : 6,465,681 B2
DATED         : October 15, 2002
INVENTOR(S)   : Masahiro Uemura et al.

It is certified that error appears in the above-identified patent and that said Letters Patent is hereby corrected as shown below:

<u>Title page,</u>
Please add the Foreign Application Priority Data as follows:

-- [30]             Foreign Application Priority Data

Dec. 26, 2000   (JP) …………………………………...2000-395770 --

Signed and Sealed this

Seventh Day of January, 2003

JAMES E. ROGAN
*Director of the United States Patent and Trademark Office*